United States Patent
Groth et al.

(10) Patent No.: US 7,183,429 B2
(45) Date of Patent: Feb. 27, 2007

(54) PREPARATION AND USE OF IMINODISUCCINIC ACID AMMONIUM METAL SALTS

(75) Inventors: Torsten Groth, Odenthal (DE); Alfred Mitschker, Odenthal (DE); Ralf-Johann Moritz, Neuss (DE); Thomas Klein, Köln (DE); Thomas Menzel, Hilden (DE); Wolfgang Wirth, Bergisch Gladbach (DE)

(73) Assignee: Lanxess Deutschland GmbH, Leverkusen (DE)

( * ) Notice: Subject to any disclaimer, the term of this patent is extended or adjusted under 35 U.S.C. 154(b) by 717 days.

(21) Appl. No.: 10/423,326

(22) Filed: Apr. 25, 2003

(65) Prior Publication Data

US 2003/0220522 A1 Nov. 27, 2003

(30) Foreign Application Priority Data

Apr. 29, 2002 (DE) ................................ 102 19 037

(51) Int. Cl.
*C07C 229/00* (2006.01)

(52) U.S. Cl. .................................................... 562/571
(58) Field of Classification Search .................. None
See application file for complete search history.

(56) References Cited

U.S. PATENT DOCUMENTS

| 6,107,518 A | 8/2000 | Groth et al. ................. 562/571 |
| 2001/0044381 A1 | 11/2001 | Dean .......................... 504/138 |

FOREIGN PATENT DOCUMENTS

| GB | 1 306 331 | 2/1973 |
| JP | 06 329606 | 11/1994 |
| JP | 06 329607 | 11/1994 |
| SU | 639 863 | 12/1978 |
| WO | 98/45251 | 10/1998 |

OTHER PUBLICATIONS

Database CA 'Online! Chemical Abstracts Service, Columbus, Ohio, US; Anzai, Ryuichi et al: "Antimicrobial mixture compositions" retrieved from STN Database accession No. 135:328372 CA XPOO2245341 RN=369603-53-2, Zusammenfassung & JP 2001 302415 A (Mitsubishi Rayon Co., Ltd., Japan) Oct. 31, 2001.

Database CA "Online! Chemical Abstracts Service, Columbus, Ohio, US; Maekawa, Kazuo et al: "Fatty acid soap-based powdered detergent compositions" retrieved from STN Database accession No. 133.311163 CA XPOO2245342 RN=302337-33-3, Zusammenfassung & JP 2000 290698 A (Asahi Denka Kogyo K. K., Japan;Coop Clean K. K.) Oct. 17, 2000.

Database CA "Online! Chemical Abstracts Service, Columbus, Ohio, US; Asakawa, Yoshiaki et al: "Water-soluble detergent builder with improved biodegradability and detergent compositions" retrieved from STN Database accession No. 124:320186 CA XPOO2245343 RN=176674-72-9 Zusammenfassung & JP 08 041490 A (Nippon Catalytic Chem Ind, Japan) Feb. 13, 19996.

*Primary Examiner*—Paul A. Zucker
(74) *Attorney, Agent, or Firm*—Michael A. Miller

(57) ABSTRACT

The invention relates to a process for the preparation of iminodisuccinic acid ammonium metal salts, characterized in that, in a first stage, maleic anhydride (MA), alkali metal hydroxide and water are mixed in the molar ratio of 2:0–3:5–30 and then ammonia is metered in in the ratio MA: ammonia 2:1.5–8, in order to obtain iminodisuccinic acid ammonium salts which, in a second stage, are reacted with metal oxides, metal hydroxides (and) or other metal salts or their mixtures to give iminodisuccinic acid ammonium metal salts of the formula 8, $$IDA(NH_4)_x(Na)_y(K)_z(Me)_m \cdot (NH_3)_n \qquad \text{Formula 8}$$

in which
IDA represents iminodisuccinic acid moiety,
$x = 0.1$–$3.9$
$y = 0$–$3$
$z = 0$–$3$
$m = 0.1$–$2$
$n = 0$–$6$
and
Me represents metals of the IInd, IIIrd and IVth main groups and of the Ist to VIIIth subgroups as well as metals of the lanthanide series, of the Periodic Table, which can occur in the oxidation states 1, 2, 3 or 4, the compounds themselves and their intermediates and the use.

4 Claims, No Drawings

PREPARATION AND USE OF IMINODISUCCINIC ACID AMMONIUM METAL SALTS

BACKGROUND OF THE INVENTION

1. Field of the Invention

The invention relates to a process for the preparation of iminodisuccinic acid ammonium metal salts by reaction of maleic anhydride, alkali metal hydroxides, ammonia and water in a first stage to give iminodisuccinic acid ammonium salts and their subsequent reaction with metal oxides, metal hydroxides or other metal salts in a second stage. The products resulting therefrom can be used to increase the availability of metal ions, e.g. in agriculture, as trace element fertilizers or slug and snail pellets, or in the ceramics industry, for surface colouring.

2. Brief Description of the Prior Art

Trace element fertilizers are used in agriculture to increase agricultural yields and to prevent plant diseases, such as apple spot (brown spots) or tomato fruiting rot (black spots) which can be traced back to a disrupted supply of calcium. Illustratively, there is employed specific calcium, magnesium, manganese, iron, copper or zinc salts of ethylenediaminetetraacetic acid (EDTA), diethylenetriaminepentaacetic acid (DTPA) or other complexing agents.

EDTA and DTPA are two conventional complexing agents which have been used for years in large amounts. However, many of the conventional complexing agents, such as EDTA and DTPA and various phosphonates and the metal complexes resulting therefrom, are not at all or only partially biodegradable; they remobilize heavy metals in surface waters and can even enter drinking water treatment, since they are not adsorbed in sewage sludges or soils.

It is therefore an important object to develop complexing agents which do not have the eco-toxicological disadvantages, such as described above.

Iminodisuccinic acid is an art-known complexing agent which is readily biodegradable and which therefore has an eco-toxicological advantage with respect to the complexing agents. Its metal salts, which can be used in agriculture and in the ceramics industry, are also biodegradable, and the preparation process is environmentally friendly, since it generates no significant solid or liquid waste and any ammonia released can be recycled in chemical processes.

GB 1 306 331 discloses the preparation of iminodisuccinic acid from maleic acid and ammonia in a molar ratio of 2:3 to 2:5 at temperatures of 60 to 155° C. For their work up, either hydrochloric acid or sodium hydroxide solution can be added. In SU 0 639 863, iminodisuccinic acid is prepared in the presence of alkali metal hydroxides from maleic acid and ammonia at a molar ratio of 2:0.8 to 2:1 at temperatures of 110 to 130° C. JP 6/329 606 discloses a three-stage process for the preparation of iminodisuccinic acid. A maleic acid derivative is first reacted with ammonia in an aqueous medium. Alkali metal or alkaline earth metal hydroxides are then added. A "maturing process" follows in the third process stage. JP 6/329 607 likewise discloses a three-stage process for the preparation of iminodisuccinic acid. In the first stage, a maleic acid derivative is again first reacted with ammonia in aqueous medium. Alkali metal or alkaline earth metal hydroxides are then added in the second stage. In the third stage, the reaction is continued after addition of further maleic acid derivative.

However, in none of the patents is a process for the preparation and the use of the iminodisuccinic acid ammonium metal salts according to the invention disclosed.

A process for the preparation of iminodisuccinate alkali metal salts and their suitability as complexing agents are known from U.S. Pat. No. 6,107,518. It is known, from U.S. Ser. No. 2001/0044381 A1, that complexes with calcium, magnesium, barium, strontium, manganese, zinc, copper and iron can be prepared.

However, none of the documents discloses a specific process for the preparation of the iminodisuccinic acid ammonium metal salts according to the invention in which not all ammonium groups are replaced with alkali metals, alkaline earth metals or heavy metals.

SUMMARY OF THE INVENTION

The present invention consequently relates to a process for the preparation of iminodisuccinic acid ammonium metal salts, characterized in that, in a first stage, maleic anhydride (MA), alkali metal hydroxide and water are mixed in the molar ratio of 2:0–3:5–30 and then ammonia is metered in the reaction mixture, in the ratio of MA: ammonia 2:1.5–8, in order to obtain iminodisuccinic acid ammonium salts of the formula 6

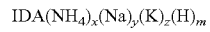  Formula 6 wherein IDA represents iminodisuccinic acid moiety, with x=0.1–4, y=0–3, z=0–3 and m=0–2, which, in a second stage, are reacted with metal oxides, metal hydroxides or other metal salts to give iminodisuccinic acid ammonium metal salts of the formula 8,

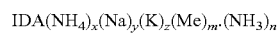  Formula 8 in which
IDA is the iminodisuccinic acid moiety
x=0.1–3.9
y=0–3
z=0–3
m=0.1–2
n=0–6 and

Me represents metals of the IInd, IIIrd and IVth main groups and of the Ist to VIIth subgroups as well as metals of the lanthanide series of the Periodic Table, which can occur in the oxidation states 1, 2, 3 or 4.

DETAILED DESCRIPTION OF THE INVENTION

In the process according to the invention, in the first stage, water, maleic anhydride (MA), alkali metal hydroxide (AlkaliOH) and ammonia (NH₃) are metered into a reactor and the maleic acid salt formed is reacted at the reaction temperatures (T) and for the reaction times (t) mentioned. In the second stage, the reaction mixture obtained is then reacted with metal oxides, metal hydroxides or other metal salts at the reaction temperatures (T) and for the reaction times (t) mentioned to give iminodisuccinic acid ammonium metal salts, optionally after addition of water and distilling off aqueous ammonia, by which highly concentrated, storage-stable and low-odour iminodisuccinic acid ammonium salt solutions can be prepared optionally after a clarifying filtration. The salts presented therein can also, by drying, be converted to solids.

The process according to the invention has the advantage that it can be carried out economically, both batchwise and continuously. As would be realized, even environmentally friendly products, in spite of all advantages, are only competitive if they can be prepared under suitably economic conditions. The process according to the invention generates virtually no waste since, after the distillation of the ammonia, this can be recycled or used in other processes and the remaining product is made use of in its entirety. Only in the clarifying filtration can small amounts of material arise, resulting from the filtration. The products according to the invention are, in addition, biodegradable. In the process and product, economics and ecology are combined with one another in a very efficient way.

In the process according to the invention, in the first stage, MA, alkali metal hydroxide and water are first mixed together in the molar ratio of MA:AlkaliOH:water 2:0–3:5–30. The mixing of the components can be carried out both under continuous and under batchwise process control. MA and alkali metal hydroxide are added to the water either simultaneously, in succession or alternately in portions. In a preferred embodiment, the pH in the metering is <11, particularly preferably <8. The metering is preferably carried out at temperatures of 50–150° C., particularly preferably at 70–120° C. The metering time depends on the embodiment. Maleic acid alkali metal salts in solution or suspension, preferably in solution, particularly preferably in concentrated solution with solids contents of more than 30 weight %, preferably more than 40 weight %, particularly preferably more than 50 weight %, are produced. After the final metering, the solutions or suspensions can be stirred.

In a particular embodiment, the molar ratio of MA:AlkaliOH=2:0. Alkali-free maleic acid solutions are thereby produced. In a further particular embodiment, the molar ratio of MA:AlkaliOH=2:0.2–2.8, preferably 2:0.5–2.5, particularly preferably 2:1.5–2.3. In a preferred embodiment, the molar ratio of MA:water=2:5.5–25, particularly preferably 2:6–20.

When the preparation is carried out in accordance with this invention, only small amounts of byproducts, such as, for example, fumaric acid and malic acid or their salts, are formed. For this reason, maleic acid or its salts are obtained with yields of more than 90%, preferably more than 95%, particularly preferably more than 98%.

With regard to a continuous process control, the continuous and simultaneous metering of a MA melt and alkali metal hydroxide solutions into a pre-charged maleic acid salt solution has proved to be particularly advantageous. In this way, even very pure and also colourless solutions can be obtained, with equally high yields.

Ammonia is metered into the suspensions or solutions comprising maleic acid or maleic acid salts formed in the course of the first stage. The molar ratio of MA:ammonia is 2:1.5–8, preferably 2:1.5–6, particularly preferably 2:1.8–5. The addition can be carried out equally well both under continuous and under batchwise process control.

In the process, MA can be used in the form of a melt, flakes or briquettes, preferably as a melt. Alkali metal hydroxides are used in bulk or in aqueous solution, e.g. in concentrations of 10–60 weight %, preferably of 20–55 weight % and particularly preferably of 25–50 weight %. Lithium hydroxide, sodium hydroxide or potassium hydroxide, and preferably sodium hydroxide or potassium hydroxide, can be chosen as alkali metal hydroxides. Ammonia can be metered in as a liquid, as a gas or as an aqueous solution.

The maleic acid ammonium salt solutions formed from MA, AlkaliOH, ammonia and water are reacted at temperatures of 70–170° C., preferably at 75–160° C., particularly preferably at 80–155° C., very particularly preferably at 85–140° C., and for reaction times of 0.1–100 h, preferably 0.7–70 h, particularly preferably 1–50 h, very particularly preferably 2–40 h. The reaction can be carried out both in continuous reactors and in batch reactors. One or more temperature levels can be introduced in a process for the reaction temperature.

The reaction is carried out under autogenous pressure. In this way, pressures of up to 50 bar, preferably up to 30 bar, particularly preferably up to 20 bar, can occur. It is possible in addition to cover the mixture with a blanket of inert gases, especially in batch reactors, thereby making possible pressures of up to 80 bar.

In a particular embodiment, alkali-free maleic acid ammonium salt solutions can surprisingly be reacted in open reactors at standard pressure without significant amounts of ammonia escaping.

A maleic acid conversion of >93%, preferably >95%, particularly preferably >98%, of the theoretical conversion is achieved through the reaction conditions.

Iminodisuccinic acid ammonium salt solutions are thus obtained in the first stage of the process according to the invention, which solutions are either used directly in the second stage for the formation of the iminodisuccinic acid ammonium metal salts or are used for the preparation of the iminodisuccinic acid ammonium metal salts if need be only after a workup.

The workup step is of considerable advantage if the preparation of the iminodisuccinic acid ammonium metal salts cannot be carried out immediately afterwards or cannot be carried out in the same manufacturing plant. Through the workup, in which the solids content and the ammonia or ammonium content are reduced through addition of water and distilling off aqueous ammonia, success is achieved in preparing highly concentrated, storage-stable and low-odour iminodisuccinic acid ammonium salt solutions. Flexible downstream production, essential for the present day, is thereby made possible.

In a preferred embodiment, the reaction mixtures obtained after reaction are thus first of all treated with water and optionally with alkali metal hydroxide and are converted, by distilling off aqueous ammonia, adjusting the pH with ammonia or aqueous ammonia, adjusting the concentration with water and optionally carrying out a clarifying filtration, to highly concentrated, storage-stable, weakly coloured and low-odour iminodisuccinic acid ammonium salt solutions.

The molar ratio of initially charged MA:AlkaliOH is 2:0–3, preferably 2:0–2. The aqueous ammonia is distilled off at temperatures of 50–150° C., preferably at 60–130° C., particularly preferably at 70–110° C., very particularly preferably at 75–105° C., and pressures of 0.1–10 bar, preferably 0.2–2 bar, over the course of 0.1–50 h, preferably 0.3–30 h, particularly preferably 0.5–25 h, very particularly preferably 0.9–20 h.

The workup can on the other hand be carried out as component of a continuous or batchwise overall process. The introduction of steam has proved to be particularly advantageous for distilling off aqueous ammonia. After workup, the solids contents are more than 20 weight %, preferably more than 30 weight %, particularly preferably more than 40 weight %. The solutions are storage-stable under the usual temperature conditions for transportation and storage, e.g. from 0–50° C., preferably 1–40° C., particularly preferably from 2–35° C.

The iminodisuccinic acid ammonium salt solutions prepared in the first stage according to the invention exhibit the following composition: iminodisuccinic acid and its salts (formula T) as a mixture of the stereoisomers (S,S-IDA, R,R-IDA and R,S-IDA) in yields of >65%, preferably >70%, particularly preferably >74%, of the theoretical yield. The combined byproducts and their salts are present in amounts of <35%, preferably <30%, particularly preferably <26%, of the theoretical amounts, in which maleic acid and its salts (formula 2) are present with <7%, preferably <5%, particularly preferably <2%, of the theoretical amount, fumaric acid and its salts (formula 3) are present with <20%, preferably <15%, particularly preferably <10%, of the theoretical amount, malic acid, as a mixture of the stereoisomers (R- and S-malic acid), and its salts (formula 4) are present with <7%, preferably <5%, particularly preferably <3%, of the theoretical amount and aspartic acid, as a mixture of the stereoisomers (R- and S-aspartic acid), and its salts (formula 5) are present with <25%, preferably <20%, particularly preferably <15%, of the theoretical amount.

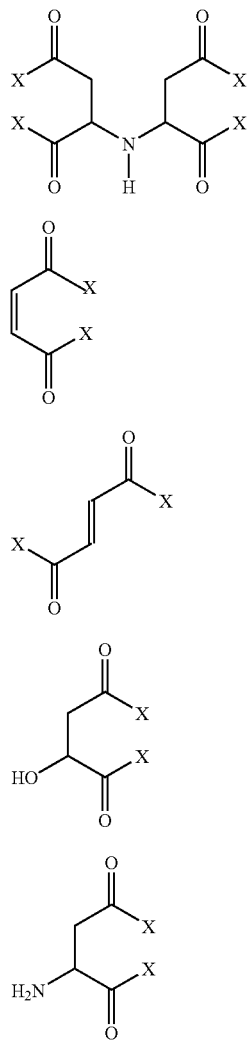

X=OH, OLi, ONa, OK, ONH$_4$

Overall, product solutions are obtained in which the stated components of the formulae 1–5 are present in overall yields of >93%, preferably >96%, particularly preferably >98%, of the theoretical yield. According to the OECD 301 E test, the biodegradation of the products after 28 days is more than 70%, generally more than 72%, frequently more than 74%. Thus, e.g., the IDA(NH$_4$)$_3$ salt is 90% degraded after just 28 days. In the OECD 302 B test, the IDAK$_2$NH$_4$ salt is 99% degraded after just 14 days and the IDA(NH$_4$)$_3$ salt is 97% degraded after 14 days.

According to the invention, the carboxyl groups of the iminodisuccinic acid and of its byproducts are, depending on the amount of ammonia introduced, particularly preferably in the ammonium salt form. According to the amount of the alkali metal hydroxide introduced in the first stage, iminodisuccinic acid ammonium salts with sodium, lithium or potassium components are obtained, for example. The preferred intermediates of the first stage according to the invention are iminodisuccinic acid ammonium salts of the formula 1

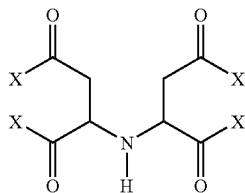

Formula 1 in which X represents OLi, ONa, OK, OH or ONH$_4$, preferably ONa, OK, OH or ONH$_4$. In the preferred form, the groups have the following molar ratio with respect to one another: ONa:OK:OH:ONH$_4$=0–3:0–3:0–2:0.1–4, preferably 0–2.5:0–2.5:0–1.5:0.5–3.5, particularly preferably 0–2.2:0–2.2:0–1.2:0.8–3.2. For the byproducts according to the invention, the molar ratios ensue corresponding to the number of their carboxyl groups.

If the iminodisuccinic acid anion is denoted by IDA, the iminodisuccinic acid ammonium salts according to the invention in the preferred form can also be described by the formula 6:

IDA(NH$_4$)$_x$(Na)$_y$(K)$_z$(H)$_m$     Formula 6 with IDA the iminodisuccinic acid moiety and x=0.1–4, y=0–3, z=0–3 and m=0–2, preferably x=0.5–3.5, y=0–2.5, z=0–2.5 and m=0–1.5, particularly preferably x=0.8–3.2, y=0–2.2, z=0–2.2 and m=0–1.2.

In particular embodiments, the particularly preferred intermediates according to the invention or their mixtures are obtained:

IDA(NH$_4$)$_3$K, IDA(NH$_4$)$_2$K$_2$, IDA(NH$_4$)K$_2$H, IDA(NH$_4$)$_2$KH and IDA(NH$_4$)K$_3$ or IDA(NH$_4$)$_3$Na, IDA(NH$_4$)$_2$Na$_2$, IDA(NH$_4$)Na$_2$H, IDA(NH$_4$)$_2$NaH and IDA(NH$_4$)Na$_3$ or IDA(NH$_4$)$_3$H and IDA(NH$_4$)$_2$H$_2$. In principle, IDA(NH$_4$)$_4$ can also be prepared in this way. These intermediates of formula 6 which can be prepared according to the present invention can be applied in the area of photography. Alkali-free iminodisuccunic acid ammonium salts are preferably used, particularly preferably IDA(NH$_4$)$_3$H, IDA(NH$_4$)$_2$H$_2$ and IDA(NH$_4$)$_4$.

Alkali-free iminodisuccinic acid ammonium salts of the formula 7

IDA(NH$_4$)$_x$(H)$_y$     Formula 7 with IDA the iminodisuccinic acid moiety and x=2–4 and y=0–2, preferably with x=2.5–3.5 and y=0.5–1.5, particularly preferably with x=2.75–3.25 and y=0.75–1.25, are particularly preferred according to the invention for the reaction in the second stage. The iminodisuccinic acid triammonium salt according to formula 7 with x=3 and y=1 is very particularly preferred according to the invention.

In the second stage of the process according to the invention, the iminodisuccinic acid ammonium salts of formula 6 or formula 7, prepared with or without workup, are reacted with metal oxides, metal hydroxides or other metal salts in aqueous solution to give the iminodisuccinic acid ammonium metal salts according to the invention of formula 8

$$IDA(NH_4)_x(Na)_y(K)_z(Me)_m(NH_3)_n \qquad \text{Formula 8}$$

in which IDA is the iminodisuccinic acid moiety and x=0.1–3.9, y=0–3, z=0–3, m=0.1–2 and n=0–6, preferably with x=0.1–3, y=0–2.5, z=0–2.5, m=0.4–1.8 and n=0–4, particularly preferably with x=0.1–2, y=0–2.2, z=0–2.2, m=0.43–1.7 and n=0–3 and very particularly preferably with x=0.5–2, y=0, z=0 or 2, m=0.43–1.6 and n=0–2.5, and Me represents metals of the IInd, IIIrd and IVth main groups and of the Ist to VIIIth subgroups as well as metals of the lanthanide series of the Periodic Table, which can occur in the oxidation states 1, 2, 3 or 4 and are preferably in the oxidation states 2 and 3, with the exception of the S,S isomers of the Mg and Ca iminodisuccinic acid ammonium metal salts. Me preferably represents the metals Mg, Ca, Sr, Ba, Ti, Zr, Cr, Mo, W, Mn, Fe, Co, Ni, Cu, Ag, Zn, Cd, Al, Sn, Pb, La or Ce and particularly preferably the metals Mg, Ca, Ti, Zr, Cr, Mo, Mn, Fe, Co, Ni, Cu, Zn, Cd, Al, Pb and Ce. In a very particularly preferable way, Me represents the metals Ti, Zr, Cr, Mo, Co, Ni, Cd, Al, Pb and Ce.

The ammonia represented in the formula 8 with $(NH_3)_n$ can exist in the free form, in the complexed form or as ammonium salt with the anions which are introduced into the product solution when using metal salts.

In a practical embodiment, the iminodisuccinic acid ammonium salt solutions prepared in the first stage are converted with metal oxides, metal hydroxides or other metal salts or their mixtures, as well as with the addition of further water and optionally with the removal by distillation of aqueous ammonia, to the iminodisuccinic acid ammonium metal salts according to the invention. The addition can be carried out continuously or portion-wise at temperatures of 10–140° C., preferably at 15–120° C. and particularly preferably at 20–100° C., over the course of 0.1–100 h, preferably 0.2–50 h, particularly preferably over the course of 0.5–25 h. The rate of addition is limited by the ability of the reaction mixture to be stirred.

The metal oxides, metal hydroxides or other metal salts or their mixtures can be added as solids, suspensions, dispersions, slurries or solutions. Auxiliaries, such as, e.g., polycarboxylic acids or polysulphonic acids, which can function as dispersing agents or threshold inhibitors, can be used with them. Environmentally friendly, biodegradable polycarboxylic acids, such as, e.g., polyamino acids, are preferred; polyaspartic acids are particularly preferred.

Alkyl- and arylamines can be added in the second reaction stage as auxiliaries for additional complexing of the metal ions. Alkylamines in which the amino group can be mono-, di- or trisubstituted are preferably used. Mono-, di-, tri- and polyamines can be used as alkylamines. Ethanolamine, diethanolamine, triethanolamine, ethylenediamine or aminosaccharides are examples. Biodegradable amines are preferably used. Alcohols, e.g. alkanols, diols, triols or polyols, can be used as additional auxiliaries. Biodegradable alcohols, e.g. ethylene glycol, can preferably be used.

Metal oxides to be used according to the invention in stage 2 of the process are, e.g., MgO, CaO, TiO, $Ti_2O_3$, $TiO_2$, $ZrO_2$, chromium(III) oxide, MnO, $Mn_2O_3$, $MnO_2$, iron(II) oxide, iron(III) oxide, cobalt(II) oxide, copper(II) oxide, zinc oxide, cadmium oxide and cerium(IV) oxide. Use may be made of metal hydroxides, such as $Mg(OH)_2$, $Ca(OH)_2$, $Zr(OH)_4$, freshly precipitated basic iron oxide, cobalt(II) hydroxide, nickel(II) hydroxide, basic copper(II) carbonate, copper(II) hydroxide, basic copper(II) phosphate, basic zinc carbonate, cadmium hydroxide, aluminium hydroxide, lanthanum(III) hydroxide and cerium(IV) hydroxide. The other metal salts are salts of inorganic and organic acids, such as, e.g., halides, sulphates, nitrates, phosphates, chlorates, perchlorates, carbonates, acetates, formates, gluconates, oxalates, sulphonates and citrates. Use is preferably made of $MgCl_2$, $CaCl_2$, zirconium acetate, basic zirconium (IV) acetate, zirconium(IV) citrate, zirconium(IV) hydrogenphosphate, chromium(II) acetate hydrate, basic chromium (III) acetate, chromium(III) chloride, chromium(III) nitrate, chromium(III) sulphate, manganese(II) acetate, manganese (II) chloride, manganese(II) nitrate, manganese(II) sulphate, iron(II) acetate, iron(II) chloride, iron(III) chloride, iron(III) citrate, iron(III) pyrophosphate hydrate, iron(III) nitrate, iron(III) oxalate, iron(II) D-gluconate, iron(III) perchlorate, iron(III) phosphate, iron(II) sulphate, iron(III) sulphate, iron (III) p-toluenesulphonate, cobalt(II) acetate, cobalt(II) carbonate, cobalt(II) chloride, cobalt(III) nitrate, cobalt(II) oxalate, cobalt(II) sulphate, nickel(II) acetate, nickel(II) chloride, nickel(II) nitrate, nickel(II), oxalate, nickel(II) perchlorate, nickel(II) sulphate, copper(I) acetate, copper(II) acetate, copper(I) chloride, copper(II) chloride, copper(II) nitrate, copper(II) perchlorate, copper(II) sulphate, silver acetate, silver nitrate, silver perchlorate, zinc acetate, zinc chloride, zinc citrate, zinc nitrate, zinc perchlorate, zinc sulphate, cadmium acetate, cadmium carbonate, cadmium chloride, cadmium nitrate, cadmium perchlorate, cadmium sulphate, basic aluminium acetate, aluminium chloride, aluminium nitrate, aluminium sulphate, tin(II) acetate, tin(II) chloride, tin(II) methanesulphonate, tin(II) sulphate, tin(IV) sulphate, basic lead(II) acetate, basic lead(II) carbonate, lead(II) nitrate, lead(II) perchlorate, lanthanum(III) acetate, lanthanum(III) carbonate, lanthanum(III) chloride, lanthanum(III) nitrate, lanthanum(III) sulphate, lanthanum(III) perchlorate, lanthanum(III) triflate, cerium(IV) ammonium sulphate, cerium(IV) ammonium nitrate, cerium(IV) perchlorate and cerium(IV) sulphate. All compounds mentioned can be used separately or as mixtures.

After the addition of the oxides, hydroxides or salts, stirring is carried out at temperatures of 10–140° C., preferably at 15–120° C. and particularly preferably at 20–100° C., over the course of 0.1–100 h, preferably 0.2–50 h, particularly preferably over the course of 0.5–25 h. Aqueous ammonia can be distilled off during the addition or during the stirring period. Adjustment to a suitable concentration of, e.g., more than 10 weight %, preferably more than 20 weight %, particularly preferably more than 30 weight %, or to a suitable pH is achieved through addition of water or aqueous ammonia. If undissolved components have remained, these can be filtered off. Use is preferably made of metal oxides, metal hydroxides or other metal salts or their mixtures for which only a clarifying filtration is necessary in this process stage. The solutions prepared according to the invention, which can also include free ammonia, can subsequently be dried, for example spray-dried. Products with a solids content of more than 75 weight %, preferably more than 80 weight %, particularly preferably more than 85 weight %, are thereby produced.

The present invention also relates to the iminodisuccinic acid ammonium metal salts of the formula 8

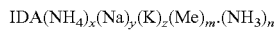

$$IDA(NH_4)_x(Na)_y(K)_z(Me)_m \cdot (NH_3)_n \qquad \text{Formula 8}$$

in which IDA is the iminodisuccinic acid moiety and $x=0.1–3.9$, $y=0–3$, $z=0–3$, $m=0.1–2$ and $n=0–6$, preferably with $x=0.1–3$, $y=0–2.5$, $z=0–2.5$, $m=0.4–1.8$ and $n=0–4$, particularly preferably with $x=0.1–2$, $y=0–2.2$, $z=0–2.2$, $m=0.43–1,7$ and $n=0–3$ and very particularly preferably with $x=0.5–2$, $y=0$, $z=0$ or 2, $m=0.43–1.6$ and $n=0–2.5$, and Me represents metals of the IInd, IIIrd and IVth main groups and of the Ist to VIIIth subgroups as well as metals of the lanthanide series of the Periodic Table, which can occur in the oxidation states 1, 2, 3 or 4 and are preferably in the oxidation states 2 and 3, with the exception of the S,S isomers of the Mg and Ca iminodisuccinic acid ammonium metal salts.

The invention relates preferably to compounds of the formula 8 in which x, y, z, m and n have the above-mentioned meanings and Me represents the metals Mg, Ca, Sr, Ba, Ti, Zr, Cr, Mo, W, Mn, Fe, Co, Ni, Cu, Ag, Zn, Cd, Al, Sn, Pb, La or Ce and particularly preferably the metals Mg, Ca, Ti, Zr, Cr, Mo, Mn, Fe, Co, Ni, Cu, Zn, Cd, Al, Pb and Ce, with the exception of the S,S isomers of the Mg and Ca iminodisuccinic acid ammonium metal salts. In a very particularly preferred embodiment, Me represents the metals Ti, Zr, Cr, Mo, Ni, Cd, Al and Pb.

The iminodisuccinic acid ammonium metal salt solutions or solids prepared according to the invention in the second stage are of the following composition: iminodisuccinic acid ammonium metal salts (formula 8) as a mixture of the stereoisomers (S,S-IDA, R,R-IDA and R,S-IDA) in yields of >65%, preferably >70%, particularly preferably >74%, of the theoretical yield. The combined byproducts and their salts are present in amounts of <35%, preferably <30%, particularly preferably <26%, of the theoretical amounts, in which maleic acid and its salts are present with <7%, preferably <5%, particularly preferably <2%, of the theoretical amount, fumaric acid and its salts are present with <20%, preferably <15%, particularly preferably <10%, of the theoretical amount, malic acid, as a mixture of the stereoisomers (R- and S-malic acid), and its salts are present with <7%, preferably <5%, particularly preferably <3%, of the theoretical amount and aspartic acid, as a mixture of the stereoisomers (R- and S-aspartic acid), and its salts are present with <25%, preferably <20%, particularly preferably <15%, of the theoretical amount.

The products are surprisingly also biodegradable and for that reason highly advantageous environmentally. In the Zahn-Wellens test, OECD 302 B, the $IDAK_2Zn_{0.5}(NH_4)_{0.5}$ salt (Example 23) was 98% degraded after just 14 days and the $IDAK_2Cu_{0.43}(NH_4)0.58$ salt (Example 24) was 99% degraded after 28 days.

The products described can be used in all fields of application in which it is necessary to increase the availability of trace elements or metal ions, e.g. in agriculture or gardening, as trace element fertilizers or slug and snail pellets, or in the ceramics industry, for surface colouring.

In fields of application in which water represents a fundamental medium, a great many metal ions form insoluble metal salts and are thus in reality unavailable for use. Upn addition of simple inorganic or organic water-soluble salts, the metal ions would in this way not reach their intended site of action. For example, it would not be possible to use the trace elements for plants and the chromophoric metal ions would not be able to penetrate deeply enough into ceramic material. With the help of complexing agents, success is now achieved in preventing the formation of insoluble metal salts and in bringing the required metal ions to their site of action. The compounds used to date are predominantly strong complexing agents which are not biodegradable or are biodegradable with difficulty, which complexing agents, on the one hand, actually almost completely prevent the formation of insoluble metal salts but, on the other hand, also partially limit the availability, e.g. of trace elements, through the strong complexing.

The availability of metal ions, for example of the trace elements Mg, Ca, Mn, Cu, Fe and Zn as trace element fertilizers, is now increased through the use of the iminodisuccinic acid ammonium metal salts according to the invention. These salts are now also available for use in the field of ceramics as metal ion carriers in the preparation of ceramics or glazings. In addition, the new salts are biodegradable and accordingly more environmentally friendly than the products to date. In biological applications, the anion can even serve additionally as nutrient source, partially as a result of the degradation. An additional advantage is that the intermediate degradation products are aspartic acid and fumaric acid, two naturally occurring compounds.

Sodium-poor mixed salts are suitable as particularly preferred trace element fertilizers based on the iminodisuccinic acid ammonium salts.

In the last decade, the colouring of tile fragments made of gres porcellanato with concentrated aqueous solutions of heavy metals has increased in importance. In the course of this, the fragments are sprayed or coated on the surface with the metal salt solution or the entire body is dipped in the solution, subsequently dried and fired. As a result of the firing, the metal complexes are converted to the corresponding coloured oxides.

The preparation of the most concentrated possible, sulphate-, nitrate- and chloride-free, solutions is important for the process (no corrosive discharge gases during the firing). A further requirement is the high capability of penetration of the metal salt solutions, which shows this in particular for gres porcellanato tiles, since these are polished after firing (marble effect). The iminodisuccinic acid metal salts according to the invention make available in solution satisfactory amounts of heavy metal down into the relatively deep layers of these tiles.

The iminodisuccinic acid ammonium salts according to the invention of the formulae 6 and 7, in particular the iminodisuccinic acid triammonium salts, surprisingly prove to be essentially ideal for this application, since chromophoric heavy metals (cobalt, nickel, iron, copper, chromium) can be held well complexed and in high concentration in solution, without chloride, nitrate and the like having to be available as counterion.

The invention is further illustrated but is not intended to be limited by the following examples in which all parts and percentages are by weight unless otherwise specified.

EXAMPLES

Preparation of Iminodisuccinic Acid Ammonium Salts

Example 1

$MA:NH_3:H_2O$ molar ratio=2:4:9, 90° C., 30 h 1 782 g=99 mol of water are introduced and heated to 80° C. 2 157.3 g=22 mol of maleic anhydride are added at 80–100° C. with stirring and cooling. After the maleic anhydride has gone into solution, the mixture is stirred for a further 0.5 h approximately. Subsequently, 748 g=44 mol of ammonia are introduced at >90° C. After the introduction of ammonia has ended, the reaction mixture is stirred at 90° C. for more than 30 h, diluted with 1 312.7 g=72.93 mol of water and cooled to ambient temperature. After a clarifying filtration, which is optionally carried out, 6 000 g of product solution are obtained with the following yields: 80.0% of theory iminodisuccinic acid ammonium salt, 14.6% of theory aspartic acid ammonium salt, 2.5% of theory fumaric acid ammonium salt, 0.6% of theory malic acid ammonium salt and 0.4% of theory maleic acid ammonium salt. The solids content (=Σ ammonium salts) is 55 weight %. The clear light-yellow solution has a density of 1.242 kg/litre and a pH of 7.3.

Example 2

MA:$NH_3$:$H_2O$ molar ratio=2:4:9, 90° C., 24 h

Implementation and amounts of this example correspond to those of Example 1. The reaction time is 24 h. The following yields are obtained: 77.9% of theory iminodisuccinic acid ammonium salt, 12.8% of theory aspartic acid ammonium salt, 3.0% of theory fumaric acid ammonium salt, 1.0% of theory malic acid ammonium salt and 3.4% of theory maleic acid ammonium salt.

Example 3

MA:$NH_3$:$H_2O$ molar ratio=2:4:9, 90° C., 36 h

Implementation and amounts of this example correspond to those of Example 1. The reaction time is 36 h. The following yields are obtained: 80.1% of theory iminodisuccinic acid ammonium salt, 15.0% of theory aspartic acid ammonium salt, 3.3% of theory fumaric acid ammonium salt, 1.1% of theory malic acid ammonium salt and 0.6% of theory maleic acid ammonium salt. The solids content (=Σ ammonium salts) is 55 weight %. The clear light-yellow solution has a density of 1.243 kg/litre and a pH of 7.03.

Example 4

MA:$NH_3$:$H_2O$ molar ratio=2:4:10, 80° C., 96 h

Water, maleic anhydride and ammonia are mixed together in the molar ratio 10:2:4, as in Example 1. The reaction time is 96 h at 80° C. After diluting and optionally carrying out a clarifying filtration, iminodisuccinic acid ammonium salt is obtained with a yield of 82.5% of theory.

Example 5

MA:$NH_3$:$H_2O$ molar ratio=2:4:10, 100° C., 9 h

Water, maleic anhydride and ammonia are mixed together in the molar ratio 10:2:4, as in Example 1. The reaction time is 9 h at 100° C. After diluting and optionally carrying out a clarifying filtration, iminodisuccinic acid ammonium salt is obtained with a yield of 77.8% of theory.

Example 6

MA:$NH_3$:$H_2O$ molar ratio=2:4:10, 110° C., 4 h

Water, maleic anhydride and ammonia are mixed together in the molar ratio 10:2:4, as in Example 1. The reaction time is 4 h at 110° C. After diluting and optionally carrying out a clarifying filtration, iminodisuccinic acid ammonium salt is obtained with a yield of 76.9% of theory.

Example 7

MA:$NH_3$:$H_2O$ molar ratio=2:4:10, 120° C., 2 h

Water, maleic anhydride and ammonia are mixed together in the molar ratio 10:2:4, as in Example 1. The reaction time is 2 h at 120° C. After diluting and optionally carrying out a clarifying filtration, iminodisuccinic acid ammonium salt is obtained with a yield of 67.9% of theory.

Example 8

MA:$NH_3$:$H_2O$ molar ratio=2:4:8, 80° C., 72 h

Water, maleic anhydride and ammonia are mixed together in the molar ratio 8:2:4, as in Example 1. The reaction time is 72 h at 80° C. After diluting and optionally carrying out a clarifying filtration, iminodisuccinic acid ammonium salt is obtained with a yield of 82.7% of theory.

Example 9

MA:$NH_3$:$H_2O$ molar ratio=2:4:6, 80° C., 60 h

Water, maleic anhydride and ammonia are mixed together in the molar ratio 6:2:4, as in Example 1. The reaction time is 60 h at 80° C. After diluting and optionally carrying out a clarifying filtration, iminodisuccinic acid ammonium salt is obtained with a yield of 82.2% of theory.

Example 10

MA:$NH_3$:$H_2O$ molar ratio=2:4:6, 120° C., 1 h

Water, maleic anhydride and ammonia are mixed together in the molar ratio 6:2:4, as in Example 1. The reaction time is 1 h at 120° C. After diluting and optionally carrying out a clarifying filtration, iminodisuccinic acid ammonium salt is obtained with a yield of 71.9% of theory.

Example 11

MA:$NH_3$:$H_2O$ molar ratio=2:6:10, 80° C., 54 h

Water, maleic anhydride and ammonia are mixed together in the molar ratio 10:2:6, as in Example 1. The reaction time is 54 h at 80° C. After diluting and optionally carrying out a clarifying filtration, iminodisuccinic acid ammonium salt is obtained with a yield of 79.0% of theory.

Example 12

MA:$NH_3$:$H_2O$ molar ratio=2:6:10, 110° C., 2 h

Water, maleic anhydride and ammonia are mixed together in the molar ratio 10:2:6, as in Example 1. The reaction time is 2 h at 110° C. After diluting and optionally carrying out a clarifying filtration, iminodisuccinic acid ammonium salt is obtained with a yield of 69.1% of theory.

Example 13

MA:NH$_3$:H20 molar ratio=2:6:8, 80° C., 42 h

Water, maleic anhydride and ammonia are mixed together in the molar ratio 8:2:6, as in Example 1. The reaction time is 42 h at 80° C. After diluting and optionally carrying out a clarifying filtration, iminodisuccinic acid ammonium salt is obtained with a yield of 77.3% of theory.

Example 14

MA:NH$_3$:H$_2$O molar ratio=2:6:6, 120° C., 1 h.

Water, maleic anhydride and ammonia are mixed together in the molar ratio 6:2:6, as in Example 1. The reaction time is 1 h at 120° C. After diluting and optionally carrying out a clarifying filtration, iminodisuccinic acid ammonium salt is obtained with a yield of 61.0% of theory.

Example 15

MA:KOH:NH$_3$:H$_2$O molar ratio=2:2:2.3:10 110° C., 8 h.

679.8 g=37.73 mol of water are introduced and heated to 80° C. Subsequently, 1 961.2 g=20 mol of MA, as a melt, and 2 244.4 g=20 mol of KOH, as a 50% solution, are metered in simultaneously at 95–105° C. over the course of 4 h. After the addition of 391.7 g=23 mol of ammonia, which is carried out at 90–105° C., the reaction mixture is stirred at 110° C. under pressure for 8 h. 5 277.1 g of reaction mixture are obtained, which can be used directly for the formation of the iminodisuccinic acid ammonium metal salts.

Example 16

200 g of water are added to the 5 277.1 g of reaction mixture from Example 15 and 230 g of aqueous ammonia are distilled off at 95–112° C. Subsequently, the mixture is adjusted to pH 7.5 with aqueous ammonia and made up with water to 5 863 g=4 248.6 ml. After a clarifying filtration at 20–40° C., an iminodisuccinic acid K$_2$ NH$_4$ salt solution with a solids content of 58.4 weight % is obtained. The following yields were found: 79.7% of theory IDAK$_2$NH$_4$ salt, 14.5% of theory aspartic acid potassium ammonium salt, 4.4% of theory fumaric acid potassium ammonium salt, 0.7% of theory maleic acid potassium ammonium salt and 0.2% of theory malic acid potassium ammonium salt.

Conversion to Iminodisuccinic Acid Ammonium Metal Salts

Example 17

Preparation of Iminodisuccinic Acid Zn NH$_4$ Salt 545.5 g of product solution from Example 1 are introduced and heated to 60° C. 81.4 g of 100% ZnO=1 mol of zinc oxide are added in 10 portions each of 8.14 g. After a total of 2.5 h, all the zinc oxide has dissolved. 626.9 g of a clear light-yellow solution are obtained, which solution is also stable on storage at 1° C. The following values are determined: pH=7.8 at 23° C.

|    | Calculated | Found |
|----|------------|-------|
| C  | 15.3%      | 15.5% |
| N  | 8.93%      | 9.0%  |
| Zn | 10.4%      | 9.9%  |

This corresponds to a compound of the formula IDA (NH$_4$)$_2$Na$_0$K$_0$Zn$_1$.(NH$_3$)$_1$. Drying this solution at 40–80° C. yielded a solid with the following values: $C_{fd}$=22.6 weight %, $N_{fd}$=12.4 weight %. This corresponds to a compound of the formula IDA(N$_4$)$_2$Na$_0$K$_0$Zn$_1$. (NH$_3$)$_{0.76}$.

Example 18

Preparation of Iminodisuccinic Acid Cu NH$_4$ Salt 545.5 g of the product solution from Example 1 are introduced and heated to 35° C. 113.5 g of 86% Cu(OH)$_2$=1 mol of copper hydroxide are added in 10 portions of 11.35 g at 35–50° C. After 1 h, all the copper hydroxide has dissolved. 659 g of a deep-blue solution are obtained, which solution is stable on storage at 1° C. The following values are determined: pH=7.1 at 23° C.

|    | Calculated | Found |
|----|------------|-------|
| C  | 14.6%      | 14.5% |
| N  | 8.5%       | 8.3%  |
| Cu | 9.6%       | 9.8%  |

This corresponds to a compound of the formula IDA (NH$_4$)$_2$Na$_0$K$_0$Cu$_1$.(NH$_3$)$_1$. The solution can be dried at 40–80° C. A solid is obtained with the following values: $C_{fd}$=22.5 weight %, $N_{fd}$=12.5 weight %. This corresponds to a compound of the formula IDA(NH$_4$)$_2$Na$_0$K$_0$Cu$_1$.(NH$_3$)$_{0.8}$.

Example 19

Preparation of Iminodisuccinic Acid Mg NH$_4$ Salt 545.5 g of product solution from Example 1 are introduced and heated to 40° C. 61.4 g of 95% Mg(OH)$_2$=1 mol of magnesium hydroxide are added in 10 portions of 6.14 g at 40–80° C. After 4 h, the magnesium hydroxide has almost completely dissolved with slight evolution of ammonia. The slightly cloudy solution is stirred for a further approximately 4 h at 80° C. and 1 h at 90° C. After a clarifying filtration, 590 g of an almost colourless solution are obtained, which solution is stable on storage at 20° C. The following values are determined: pH=9.2 at 24° C.

|    | Calculated | Found |
|----|------------|-------|
| C  | 15.8%      | 16.4% |
| N  | 9.2%       | 7.9%  |
| Mg | 4.0%       | 3.9%  |

This corresponds to a compound of the formula IDA (NH$_4$)$_2$Na$_0$K$_0$Mg$_1$.(NH$_3$)$_1$. The solution can be dried at 40–80° C. A solid is obtained with the following values: $C_{fd}$=26.4 weight %, $N_{fd}$=10.7 weight %. This corresponds to a compound of the formula IDA(NH$_4$)$_{1.78}$Na$_0$K$_0$Mg$_1$. (NH$_3$)$_0$.

Example 20

Preparation of Iminodisuccinic Acid Ca NH$_4$ Salt 545.5 g of product solution from Example 1 are introduced and heated to 60° C. 77.2 g of 96% Ca(OH)$_2$=1 mol of calcium hydroxide are added in 10 portions of 7.72 g at approximately 60–65° C. After 8 portions and approximately 2.5 h, an almost clear solution is present. After a further 2 portions and approximately 3 h, a cloudy solution is obtained. After a clarifying filtration, 605 g of an almost colourless solution are obtained, which solution is stable on storage at 20° C. The following values are determined pH=9.7 at 24° C.

|    | Calculated | Found |
|----|-----------|-------|
| C  | 15.4%     | 15.8% |
| N  | 9.0%      | 8.1%  |
| Ca | 6.4%      | 6.2%  |

This corresponds to a compound of the formula IDA(NH$_4$)$_2$Na$_0$K$_0$Ca$_1$.(NH$_3$)$_1$. The solution can be dried at 40–80° C. A solid is obtained with the following values: C$_{fd}$=26.6 weight %, N$_{fd}$=10.0 weight %. This corresponds to a compound of the formula IDA(NH$_4$)$_{1.58}$Na$_0$K$_0$Ca$_1$.(NH$_3$)$_0$.

Example 21

Preparation of Iminodisuccinic Acid Mn NH$_4$ Salt 545.5 g of product solution from Example 1 are introduced and heated to 60° C. 258 g of (CH$_3$CO$_2$)$_2$Mn.2H$_2$O=1 mol of manganese acetate dihydrate are added in 2 portions of 129 g at 60° C. After approximately 3 h, the manganese acetate dihydrate has dissolved. After a clarifying filtration, 785 g of a clear solution are obtained, which solution is stable on storage at 20° C. The following values are determined: pH=5.5 at 24° C.

|    | Calculated | Found |
|----|-----------|-------|
| C  | 18.3%     | 18.5% |
| N  | 7.0%      | 7.0%  |
| Mn | 6.8%      | 6.7%  |

This corresponds to a compound of the formula IDA(NH$_4$)$_2$Na$_0$K$_0$Mn$_1$.(NH$_3$)$_1$. The solution can be dried at 40–80° C. A solid is obtained with the following values: C$_{fd}$=25.4 weight %, N$_{fd}$=9.9 weight %. This corresponds to a compound of the formula IDA(NH$_4$)$_2$Na$_0$K$_0$Mn$_1$.(NH$_3$)$_1$. The excess ammonia is present in this case as ammonium acetate.

Example 22

Preparation of Iminodisuccinic Acid Zn NH$_4$ Salt 545.5 g of product solution from Example 1 are introduced and heated to 60° C. 130.24 g of ZnO=1.6 mol of zinc oxide are added in 16 portions of 8.14 g at 60–70° C. After approximately 4.5 h, the zinc oxide has dissolved, after the temperature had been briefly raised to 80° C. After a clarifying filtration, 663 g of a clear solution are obtained, which solution is stable on storage at 20° C. The following values are determined:

|    | Calculated | Found |
|----|-----------|-------|
| C  | 14.2%     | 14.6% |
| N  | 8.3%      | 8.3%  |
| Zn | 15.5%     | 15.0% |

This corresponds to a compound of the formula IDA(NH$_4$)$_{0.8}$Na$_0$K$_0$Zn$_{1.6}$.(NH$_3$)$_{2.2}$. The solution can be dried at 40–80° C. A solid is obtained with the following values: C$_{fd}$=21.3 weight %, N$_{fd}$=11.9 weight %. This corresponds to a compound of the formula IDA(NH$_4$)$_{0.8}$Na$_0$K$_0$Zn$_{1.6}$.(NH$_3$)$_{2.03}$.

Example 23

Preparation of IDA(NH$_4$)$_{0.5}$Na$_0$K$_2$Zn$_{0.5}$.(NH$_3$)$_0$ Salt 527.7 g=1 mol of iminodisuccinic acid K$_2$ (NH$_4$)$_{1.3}$ crude product from Example 15 are introduced and heated to 50° C. 40.7 g=0.5 mol of zinc oxide are added portionwise. A total of 500 g of aqueous ammonia, comprising 13.6 g of ammonia, are distilled off at 80–115° C. from the cloudy yellow solution comprising the IDA(NH$_4$)$_1$Na$_0$K$_2$Zn$_{0.5}$.(NH$_3$)$_{0.3}$. During the distillation, a corresponding amount of water is readded. After the distillation, the mixture is made up to 595.2 g with water. After a clarifying filtration, a clear solution is obtained, which solution is stable on storage at 1° C. over several weeks.

Example 24

Preparation of IDA(NH$_4$)$_{0.58}$Na$_0$K$_2$Cu$_{0.43}$.(NH$_3$)$_0$ Salt 527.7 g=1 mol of iminodisuccinic acid K$_2$ (NH$_4$)1.3 crude product from Example 15 are introduced and heated to 60° C. 48.8 g of 86% Cu(OH)$_2$=0.43 mol of copper hydroxide are added in 5 portions of 9.76 g at 60° C. A total of 300 g of aqueous ammonia, comprising 12.17 g of ammonia, are distilled off at 80–115° C. from the cloudy blue solution comprising the IDA(NH$_4$)$_{114}$Na$_0$K$_2$Cu$_{0.43}$.(NH$_3$)$_{0.16}$ salt. During the distillation, a corresponding amount of water is readded. After the distillation, the mixture is made up to 593.6 g with water. After a clarifying filtration, a clear solution is obtained, which solution is stable on storage.

Further Examples

The following additional products can be prepared analogously to formula 8=IDA(NH$_4$)$_x$(Na)$_y$(K)$_z$(Me)$_m$.(NH$_3$)$_n$:

| Example | Me | x   | y | z | m   | n   |
|---------|-----|-----|---|---|-----|-----|
| 25      | Al  | 1   | 0 | 0 | 1   | 2   |
| 26      | Al  | 2.5 | 0 | 0 | 0.5 | 0.5 |
| 27      | Cr  | 1   | 0 | 0 | 1   | 2   |
| 28      | Cr  | 2.5 | 0 | 0 | 0.5 | 0.5 |
| 29      | Fe$^{II}$  | 2   | 0 | 0 | 1   | 1   |
| 30      | Fe$^{II}$  | 3   | 0 | 0 | 0.5 | 0   |
| 31      | Fe$^{III}$ | 1   | 0 | 0 | 1   | 2   |
| 32      | Fe$^{III}$ | 2.5 | 0 | 0 | 0.5 | 0.5 |
| 33      | Co  | 2   | 0 | 0 | 1   | 1   |
| 34      | Co  | 3   | 0 | 0 | 0.5 | 0   |
| 35      | Ni  | 2   | 0 | 0 | 1   | 1   |
| 36      | Ni  | 3   | 0 | 0 | 0.5 | 0   |
| 37      | Ag  | 3   | 0 | 0 | 1   | 0   |
| 38      | Ag  | 2   | 0 | 0 | 2   | 1   |
| 39      | Cd  | 2   | 0 | 0 | 1   | 1   |

-continued

| Example | Me | x | y | z | m | n |
|---|---|---|---|---|---|---|
| 40 | Cd | 3 | 0 | 0 | 0.5 | 0 |
| 41 | Pb | 2 | 0 | 0 | 1 | 1 |
| 42 | Pb | 3 | 0 | 0 | 0.5 | 0 |
| 43 | La | 2 | 0 | 0 | 1 | 1 |
| 44 | La | 3 | 0 | 0 | 0.5 | 0 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the preparation of iminodisuccinic acid ammonium metal salts, comprising:

in a first stage, mixing maleic anhydride (MA), alkali metal hydroxide and water in a molar ratio of 2:0–3:5–30 and then metering ammonia into the resulting reaction mixture in a molar ratio of MA:ammonia 2:1.5–8, in order to obtain iminodisuccinic acid ammonium salts of the formula 6

$$IDA(NH_4)_x(Na)_y(K)_z(H)_m \qquad \text{Formula 6}$$

wherein IDA represents iminodisuccinic acid moiety, with $x=0.1–4$, $y=0–3$, $z=0–3$ and $m=0–2$, in a second stage, reacting the iminodisuccinic acid ammonium salts with metal oxides, metal hydroxides or metal salts or their mixtures to give iminodisuccinic acid ammonium metal salts of the formula 8, $$IDA(NH_4)_x(Na)_y(K)_z(Me)_m \cdot (NH_3)_n \qquad \text{Formula 8}$$

in which
IDA is the iminodisuccinic acid moiety
$x=0.1–3.9$
$y=0–3$
$z=0–3$
$m=0.1–2$
$n=0–6$
and Me represents metals of the IInd, IIIrd and IVth main groups and of the Ist to VIIIth subgroups as well as metals of the lanthanide series of the Periodic Table, which can occur in the oxidation states 1, 2, 3 or 4.

2. Process according to claim 1 wherein, ammonia is metered into the reaction mixture which is in the form of suspensions or solutions comprising maleic acid or maleic acid salt(s) in the MA:ammonia molar ratio of 2:1.5–8.

3. Iminodisuccinic acid ammonium metal salts of the formula 8

$$IDA(NH_4)_x(Na)_y(K)_z(Me)_m(NH_3)_n \qquad \text{Formula 8}$$

wherein
IDA is the iminodisuccinic acid moiety
$x=0.1–3.9$
$y=0–3$
$z=0–3$
$m=0.1–2$
$n=0–6$,
and Me represents metals of the IInd, IIIrd and IVth main groups and of the Ist to VIIIth subgroups as well as metals of the lanthanide series of the Periodic Table, which can occur in the oxidation states 1, 2, 3 or 4, with the exception of the S,S isomers of the Mg and Ca iminodisuccinic acid ammonium metal salts.

4. Iminodisuccinic acid ammonium metal salts of the formula (8) according to claim 3, wherein Me represents Mg, Ca, Sr, Ba, Ti, Zr, Cr, Mo, W, Mn, Fe, Co, Ni, Cu, Ag, Zn, Cd, Al, Sn, Pb, La or Ce, with the exception of the S,S isomers of the Ca and Mg iminodisuccinic acid ammonium metal salts.

* * * * *